US00PP29485P3

(12) United States Plant Patent
Ammerlaan

(10) Patent No.: US PP29,485 P3
(45) Date of Patent: Jul. 10, 2018

(54) *ALOE* PLANT NAMED 'DEMI'

(50) Latin Name: *Aloe rauhii*
Varietal Denomination: DEMI

(71) Applicant: Johannes Hendrikus Adrianus Ammerlaan, Bleiswijk (NL)

(72) Inventor: Johannes Hendrikus Adrianus Ammerlaan, Bleiswijk (NL)

(73) Assignee: Ovata B.V., Bleiswijk (NL)

( * ) Notice: Subject to any disclaimer, the term of this patent is extended or adjusted under 35 U.S.C. 154(b) by 0 days.

(21) Appl. No.: 15/731,280

(22) Filed: May 17, 2017

(65) Prior Publication Data

US 2018/0084701 P1 Mar. 22, 2018

(51) Int. Cl.
*A01H 5/12* (2018.01)

(52) U.S. Cl.
USPC ..... Plt./373
CPC ..... *A01H 5/12* (2013.01)

(58) Field of Classification Search
USPC ..... Plt./373, 372
CPC ..... A01H 5/12
See application file for complete search history.

(56) References Cited

PUBLICATIONS

PLUTO UPOVROM Citation for 'Demi' as per QZ PBR 20162299; Dec. 15, 2016; 1 page.*

* cited by examiner

*Primary Examiner* — Kent L Bell
(74) *Attorney, Agent, or Firm* — Samuel R. McCoy, Jr.

(57) ABSTRACT

A new and distinct *Aloe rauhii* cultivar named 'DEMI' which is characterized by a flattened globular profile with foliage arranged in a short and compact rosette, strong broad ovate to near deltoid foliage with a long apiculate apex, dark green general coloration of the leaf, and foliage that is densely covered with raised, elongated papillae that are tightly arranged in distinct longitudinal rows which cover the entirety of both leaf surfaces. The new variety has shown to be uniform and stable in the resulting generations from asexual propagation.

4 Drawing Sheets

Latin name of the genus and species: The Latin name of the genus and species of the novel variety disclosed herein is *Aloe rauhii.*

Variety denomination: The inventive variety of *Aloe* disclosed herein has been given the variety denomination 'DEMI'.

This application claims priority to the Community Plant Variety Rights application number 2016/2299, filed Sep. 21, 2016, which is herein incorporated by reference.

BACKGROUND OF THE INVENTION

Parentage: 'DEMI' originated as a naturally occurring, whole-plant mutation of the species *Aloe rauhii* (not a named variety or cultivar, and not patented). In 2009, the inventor discovered the mutation at a commercial greenhouse in Bleiswijk, The Netherlands, growing amongst a crop of the species unnamed, unpatented *Aloe rauhii* plant. The mutation was noted for its dark green foliage with elongated papillae, white in color, which create a pattern of dense longitudinal striping on both the upper and lower leaf surfaces. The mutation was isolated for further observation and subsequent commercialization.

Asexual Reproduction: Asexual reproduction of the new cultivar 'DEMI', by way of rooting side shoots harvested from the claimed plant, was first initiated in 2009 at the inventor's commercial greenhouse in Bleiswijk, The Netherlands. The claimed plant has since been asexually propagated by way of meristematic tissue culture propagation.

Through 13 subsequent generations, the unique features of this cultivar have proven to be stable and true to type.

SUMMARY OF THE INVENTION

The cultivar 'DEMI' has not been observed under all possible environmental conditions. The phenotype may vary somewhat with variations in environment such as temperature, day length, and light intensity, without, however, any variance in genotype. The following traits have been repeatedly observed and are determined to be the unique characteristics of 'DEMI'. These characteristics in combination distinguish 'DEMI' as a new and distinct *Aloe rauhii* cultivar:

1. 'DEMI' exhibits a flattened globular profile with foliage arranged in a short, compact rosette; and
2. 'DEMI' exhibits strong foliage with a broad ovate to near deltoid shape and a long apiculate apex; and
3. 'DEMI' exhibits dark green foliage; and
4. 'DEMI' exhibits foliage that is densely covered with raised elongated papillae, white in general coloration, on both the adaxial and abaxial surfaces; and
5. 'DEMI' exhibits an abundance of papillae which are tightly arranged longitudinal rows across the entire adaxial and abaxial leaf surfaces.

BOTANICAL DESCRIPTION OF THE PLANT

Figure 1:
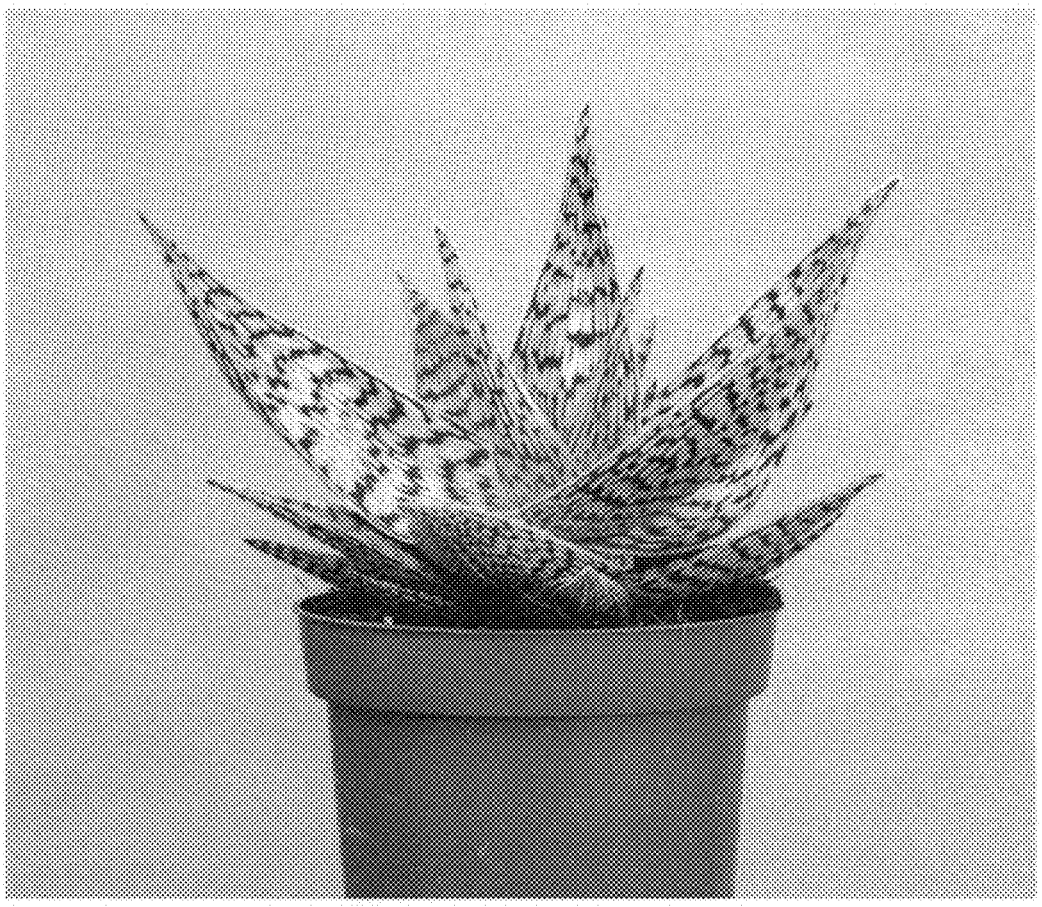
FIG. 1 illustrates, as nearly true as it is reasonably possible to make the same in color photographs of this type, an exemplary plant of 'DEMI' grown in a commercial greenhouse in Bleiswijk, The Netherlands. This plant is approximately 12 months old, shown planted in a 12 cm container.
Figure 2:
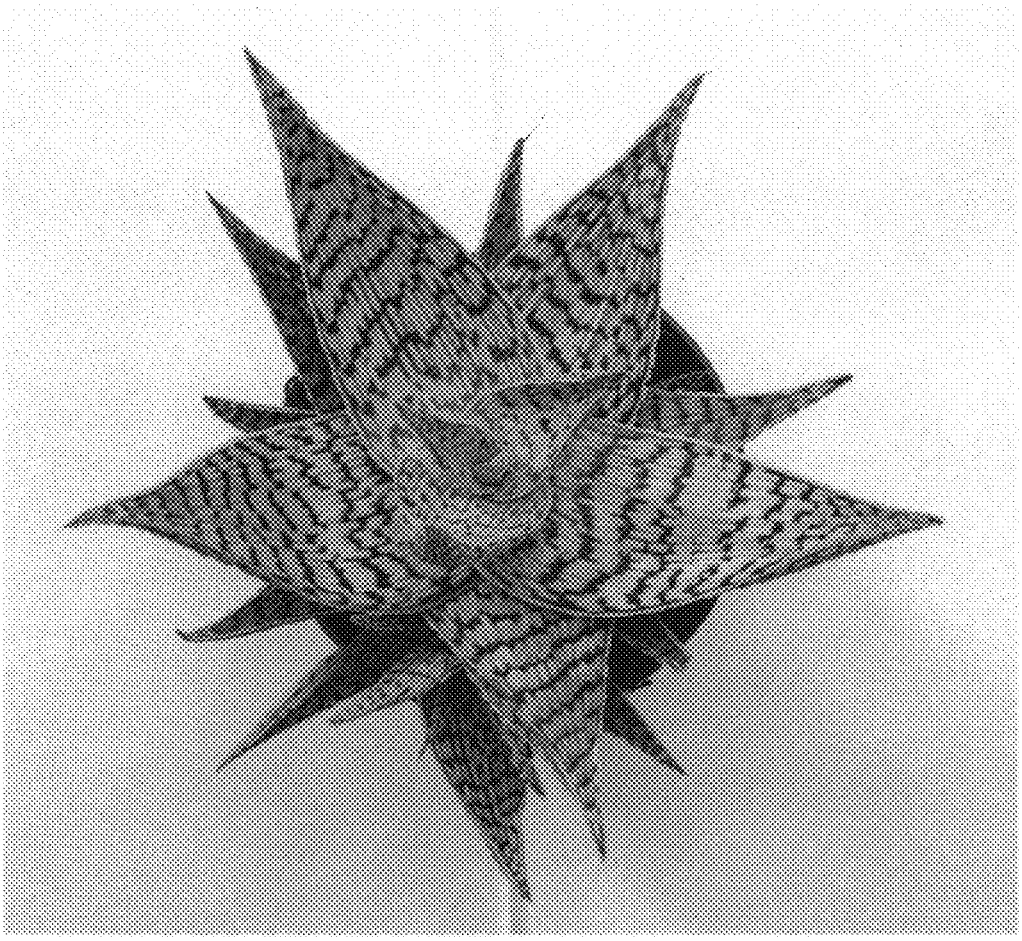
FIG. 2 illustrates, as nearly true as it is reasonably possible to make the same in color photographs of this type, the typical foliage arrangement of 'DEMI'.
Figure 3:
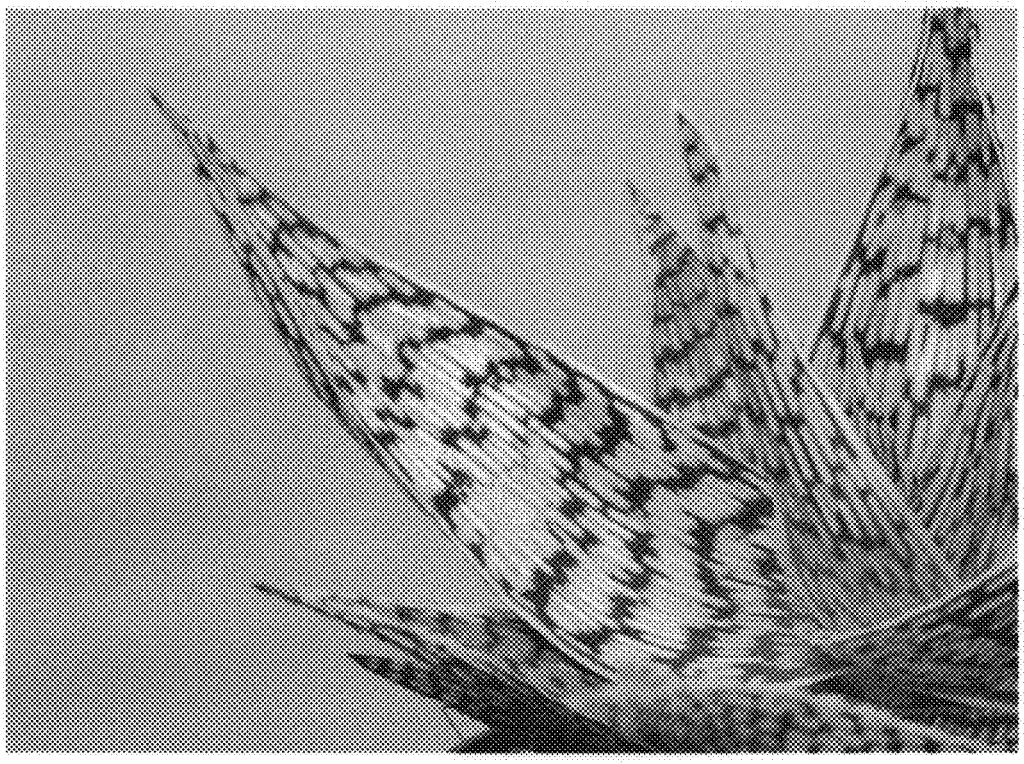
FIG. 3 illustrates, as nearly true as it is reasonably possible to make the same in color photographs of this type, the adaxial surface of the mature foliage 'DEMI'.
Figure 4:
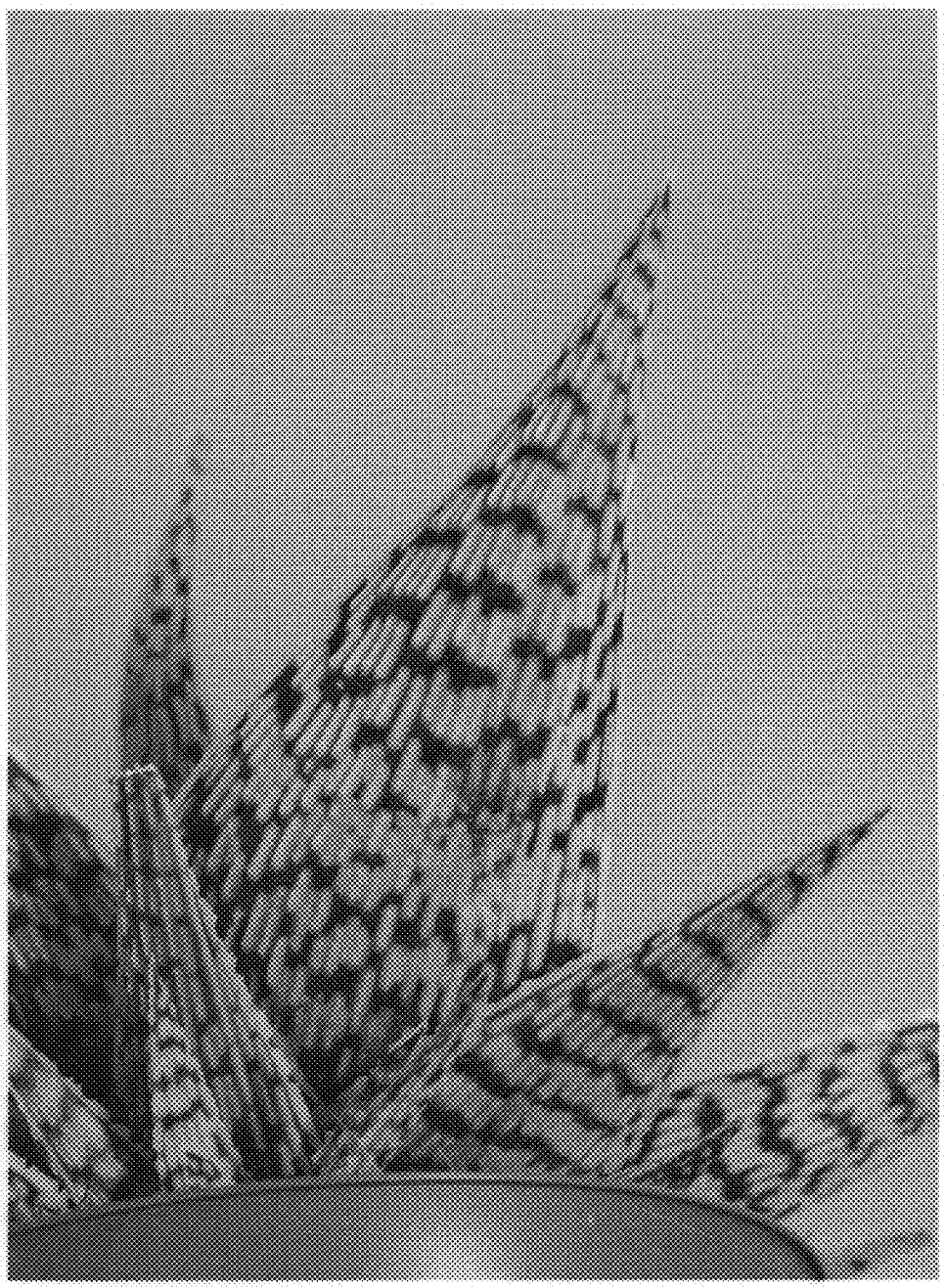
FIG. 4 illustrates, as nearly true as it is reasonably possible to make the same in color photographs of this type, the abaxial surface of the mature foliage 'DEMI'.

The following observations and measurements made in April of 2017 describe averages from a sample set of six specimens of 12 months old 'DEMI' plants grown in 12 cm nursery containers at a commercial greenhouse in Bleiswijk, The Netherlands. Plants were produced using conventional greenhouse production protocols for *Aloe* which consisted of minimal irrigation and fertilizer applications. No pest or disease control measures were utilized in production. Plants were grown under shade (approximately 12,500 lux) and no photoperiodic treatments or artificial light was given to the plants.

Those skilled in the art will appreciate that certain characteristics will vary with older or, conversely, with younger plants. 'DEMI' has not been observed under all possible environmental conditions. Where dimensions, sizes, colors and other characteristics are given, it is to be understood that such characteristics are approximations or averages set forth as accurately as practicable. The phenotype of the variety may differ from the descriptions set forth herein with variations in environmental, climatic and cultural conditions. Color notations are based on *The Royal Horticultural Society Colour Chart*, The Royal Horticultural Society, London, 2015 (sixth edition).

A botanical description of 'DEMI' and a comparison with the parent and closest known comparator a plant of, *Aloe rauhii*, is provided below.

Plant description:

*Growth habit*.—Succulent perennial with foliage growing in a non-branched basal rosette.

*Plant shape*.—Flattened globular.

*Height from soil level to top of foliar plane*.—13.7 cm.

*Plant spread*.—Average of 20.5 cm.

*Growth rate*.—Low.

*Propagation*.—Type — Leaf cuttings and meristematic tissue culture. Time to initiate rooting — Approximately 30 days at 21 degrees Celsius. Crop time — Approximately 12 months to produce a marketable plant in a 7 cm container.

*Disease and pest resistance or susceptibility*.—Neither resistance nor susceptibility to typical *Aloe rauhii* pests and diseases has been observed.

*Environmental tolerances*.—Adapt to, at least, USDA Zones 10 to 12 and temperatures as high as 40 degrees Celsius; low tolerance to rain; high tolerance to wind.

Root system:

*General*.—Fine, well-branched fibrous roots.

Stems:

*Branching habit*.—Leaves in a non-branching basal rosettes; no main branches or lateral branches present.

Foliage:

*Arrangement*.—Rosette.

*Division*.—Simple.

*Attachment*.—Sessile.

*Quantity*.—Approximately 16 leaves per rosette.

*Shape*.—Thick, succulent leaves; ovate to near deltoid in shape.

*Strength*.—Strong.

*Dimensions*.—12.9 cm long, 5.3 cm wide, and 0.9 cm thick, on average.

*Aspect*.—Slightly concave.

*Attitude*.—Slightly curved upward.

*Apex*.—Long apiculate.

*Base*.—Broad cuneate.

*Margin*.—Finely irregular dentate; not undulated or lobed.

*Texture, adaxial surface*.—Glabrous and heavily covered with narrow, elongated papillae, each approximately 7.0 mm long and 2.0 mm high.

*Texture, abaxial surface*.—Glabrous and heavily covered with narrow, elongated papillae, each approximately 7.0 mm long and 2.0 mm high.

*Luster, adaxial surface*.—Slightly to moderately glossy.

*Luster, abaxial surface*.—Slightly glossy.

*Color*.—Juvenile foliage, adaxial surface — Green, nearest to RHS NN137A, and fading to yellow-green towards the base, nearest to RHS 145B; papillae are greyed-green, nearest to in between RHS 193A to 193D. Juvenile foliage, abaxial surface — Green, nearest to RHS NN137A, and fading to yellow-green towards the base, nearest to RHS 145B; papillae are greyed-green, nearest to in between RHS 193A to 193D. Mature foliage, adaxial surface — Nearest to in between green, RHS 139A, and yellow-green, RHS 147A; fading to lighter yellow-green at the base, nearest to in between RHS 146A to 146D; papillae are greyed-green, nearest to in between RHS 193A to 193D. Mature foliage, abaxial surface — Nearest to in between green, RHS 139A, and yellow-green, RHS 147A; fading to lighter yellow-green at the base, nearest to in between RHS 146A to 146D; papillae are greyed-green, nearest to in between RHS 193A to 193D.

*Venation*.—No venation is visible.

*Petiole*.—No petiole; leaves are sessile.

Inflorescence: No flowering has been observed to date.

COMPARISONS WITH THE PARENT PLANT

Plants of the new cultivar 'DEMI' differ from the parent, *Aloe rauhii* (unnamed and not patented), in the following characteristics described in Table 1 below.

TABLE 1

| Characteristic | 'DEMI' | *Aloe rauhii* |
|---|---|---|
| Plant height. | Shorter than the parent; more compact. | Taller than 'DEMI'; less compact. |
| Leaf shape. | Broad ovate to near deltoid, with a long apiculate apex. | Lanceolate with an acute apex; narrower than 'DEMI' at the leaf base. |

TABLE 1-continued

| Characteristic | 'DEMI' | *Aloe rauhii* |
|---|---|---|
| Leaf margin. | Finely irregular dentate. | Cartilaginous with many spines. |
| Leaf papillae. | Papilla are raised. | Papilla are not raised. |

COMPARISONS WITH THE CLOSEST KNOWN COMPARATOR

Plants of the new cultivar 'DEMI' differ from the parent, *Aloe rauhii* 'Snowflake' (not patented), in the following characteristics described in Table 2 below.

TABLE 2

| Characteristic | 'DEMI' | 'Snowflake' |
|---|---|---|
| Plant height. | Shorter than the 'Snowflake'; more compact. | Taller than 'DEMI'; less compact. |
| Leaf length. | Shorter than 'Snowflake'. | Longer than 'DEMI'. |
| Occurrence of leaf papillae. | An abundance of papillae tightly arranged into numerous longitudinal rows across the entire leaf. | Fewer papillae, irregularly arranged into loose transverse rows. |
| Leaf margin. | Finely irregular dentate. | Cartilaginous with many spines. |

That which is claimed is:

1. A new and distinct variety of *Aloe rauhii* plant named 'DEMI', substantially as described and illustrated herein.

* * * * *